(12) United States Patent
Haydar et al.

(10) Patent No.: US 7,939,520 B2
(45) Date of Patent: May 10, 2011

(54) AMINOAZACYCLYL-3-SULFONYLINDAZOLES AS 5-HYDROXYTRYPTAMINE-6 LIGANDS

(75) Inventors: Simon Nicolas Haydar, Newton, PA (US); Patrick Andrae, Jamesburg, NJ (US)

(73) Assignee: Wyeth LLC, Five Giralda Farms, Madison, NJ (US)

( * ) Notice: Subject to any disclaimer, the term of this patent is extended or adjusted under 35 U.S.C. 154(b) by 333 days.

(21) Appl. No.: 12/119,837

(22) Filed: May 13, 2008

(65) Prior Publication Data
US 2008/0293688 A1    Nov. 27, 2008

Related U.S. Application Data

(60) Provisional application No. 60/930,186, filed on May 15, 2007.

(51) Int. Cl.
*A61K 31/416* (2006.01)
*A61K 31/454* (2006.01)
*C07D 401/10* (2006.01)
*C07D 403/10* (2006.01)
*A61P 25/18* (2006.01)

(52) U.S. Cl. ............... 514/210.21; 514/322; 514/403; 546/199; 548/361.5

(58) Field of Classification Search .............. None
See application file for complete search history.

(56) References Cited

U.S. PATENT DOCUMENTS
6,380,199 B1    4/2002  Reavill et al. ............ 514/252.13

FOREIGN PATENT DOCUMENTS
WO    WO 2004/074243 A2    9/2004
WO    WO 2007/032833 A     2/2007

OTHER PUBLICATIONS

Bentley, J.C. et al. "Investigation of stretching behaviour induced by the selective 5-HT6 receptor antagonist, Ro 04-6790, in rats." Br J Pharmacol. 1999; 126(7):1537-42.
Branchek, T.A. et al. "5-HT6 receptors as emerging targets for drug discovery". Annu Rev Pharmacol Toxicol. 2000; 40:319-3.
Dawson L.A., et al. "In vivo effects of the 5-HT6 antagonist SB-271046 on striatal and frontal cortex extracellular concentrations of noradrenaline, dopamine, 5-HT, glutamate and aspartate." Br J Pharmacol. 2000; 130(1):23-6.
Ernst, M. et al. "DOPA decarboxylase activity in attention deficit hyperactivity disorder adults. A [fluorine-18]fluorodopa positron emission tomography study." J Neurosci. 1998; 18(15):5901-7.
Kohen, R. et al. "Cloning, characterization, and chromosomal localization of a human 5-HT6 serotonin receptor." J Neurochem. 1996; 66(1):47-56.
Lowry et al. "Protein measurement with the Folin phenol reagent." J Biol Chem. 1951;193(1):265-75.

Gerard, C. et al. "Immuno-localization of serotonin 5-HT6 receptor-like material in the rat central nervous system". Brain Res. 1997; 746(1-2):207-19.
Monsma, F. J. et al. "Cloning and expression of a novel serotonin receptor with high affinity for tricyclic psychotropic drugs." Mol Pharmacol. 1993; 43(3):320-7.
Reavill, C. et al. "The therapeutic potential of 5-HT6 receptor antagonists". Curr Opin Investig Drugs. 2001; 2(1):104-9.
Rogers, D. C. et al. "The selective 5HT6 receptor antagonist, sb-271046-a, enhances performance of maze tasks in the rat." Society of Neuroscience, Abstracts, 2000.
Routledge,C. et al. "Characterization of SB-271046: a potent, selective and orally active 5-HT6 receptor antagonist." Br J Pharmacol. 2000; 130(7):1606-12.
Ruat, M. et al. "A novel rat serotonin (5-HT6) receptor: molecular cloning, localization and stimulation of cAMP accumulation". Biochem Biophys Res Commun. 1993;193(1):268-76.
Ward, R.P. et al. "Localization of serotonin subtype 6 receptor messenger RNA in the rat brain by in situ hybridization histochemistry." Neuroscience. 1995; 64(4):1105-11.
Woolley, M.L. et al. "Reversal of a cholinergic-induced deficit in a rodent model of recognition memory by the selective 5-HT6 receptor antagonist, Ro 04-6790." Psychopharmacology (Berl). 2003; 170(4):358-67.
Schreiber, R., et al., "5-HT$_6$ Receptors as Targets for the Treatment of Cognitive Deficits in Schizophrenia", The Receptors: The Serotonin Receptors, 2006, pp. 495-515, Appendix A.
Holenz, J., et al., "Medicinal Chemistry Strategies to 5-HT$_6$ Receptor Ligands as Potential Cognitive Enhancer and Antiobesity Agents", Drug Discovery Today, 2006, pp. 283-299, vol. 11, Appendix 2.
Ernst, M., et al., "DOPA Decarboxylase Activity in Attention Deficit Hyperactivity Disorder Adults. A [Fluorine-18]Fluorodopa Positron Emission Tomographic Study", The Journal of Neuroscience, 1998, pp. 5901-5907, vol. 18, Appendix 4.
Mitchell, E., et al., "5-HT$_6$ Receptors: A Novel Target for Cognitive Enhancements", Pharmacology & Therapeutics, 2005, pp. 320-333, vol. 108, Appendix 5.
Schechter, L. E., et al., "Neuropharmacological Profile of Novel and Selective 5-HT$_6$ Receptor Agonists: WAY-181187 and WAY-208466", Neuropsychopharmacology, 2008, pp. 1323-1335, vol. 33, Appendix 6.
Messina, et al., "Association of the 5-HT$_6$ Receptor Gene Polymorphism C267T with Parkinson's Disease", Neurology, 2002, pp. 828-829, vol. 58, Appendix 7.
Routledge, C., et al., "Characterization of SB-271046: A Potent, Selective and Orally Active 5-HT$_6$ Receptor Antagonist", British Journal of Pharmacology, 2000, pp. 1606-1612, vol. 130, Appendix 8.
Pullagurla, M., et al., "Modulation of the Stimulus Effects of (+) amphetamine by the 5-HT6 Antagonist MS-245", Pharmacology, Biochemistry and Behavior, 2004, pp. 263-268, vol. 78, Appendix 9.

*Primary Examiner* — Kamal A Saeed
(74) *Attorney, Agent, or Firm* — Jennifer A. Kispert; Richard V. Zanzalari

(57) ABSTRACT

The present invention provides a compound of formula I and the use thereof in the therapeutic treatment of disorders related to or affected by the 5-HT6 receptor.

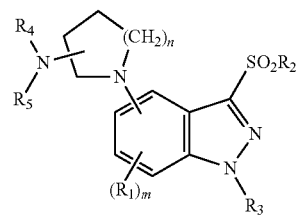

(I)

29 Claims, No Drawings

AMINOAZACYCLYL-3-SULFONYLINDAZOLES AS 5-HYDROXYTRYPTAMINE-6 LIGANDS

CROSS-REFERENCE TO RELATED APPLICATIONS

This application claims the benefit of U.S. Provisional Application No. 60/930,186, filed May 15, 2007, the entire contents of which are incorporated herein by reference.

FIELD

The present invention relates to aminoazacyclyl-3-sulfonylindazole compounds, compositions containing these compounds, and methods of their use in the treatment of central nervous system disorders related to or affected by the 5-HT6 receptor. One potential therapeutic use of modulators of 5-HT6 receptor function is in the enhancement of cognition and memory in human diseases such as Alzheimer's.

BACKGROUND

Serotonin (5-Hydroxytryptamine)(5-HT) receptors play a critical role in many physiological and behavioral functions in humans and animals. These functions are mediated through various 5-HT receptors distributed throughout the body. There are now approximately fifteen different human 5-HT receptor subtypes that have been cloned, many with well-defined roles in humans. One of the most recently identified 5-HT receptor subtypes is the 5-HT6 receptor, first cloned from rat tissue in 1993 (Monsma, F. J.; Shen, Y.; Ward, R. P.; Hamblin, M. W. *Molecular Pharmacology* 1993, 43, 320-327) and subsequently from human tissue (Kohen, R.; Metcalf, M. A.; Khan, N.; Druck, T.; Huebner, K.; Sibley, D. R. *Journal of Neurochemistry* 1996, 66, 47-56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C. *Biochemical Biophysical Research Communications* 1993, 193, 268-276). The receptor is found almost exclusively in the central nervous system (CNS) areas both in rat and in human. In situ hybridization studies of the 5-HT6 receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64, 1105-1111).

There are many potential therapeutic uses for 5-HT6 ligands in humans based on direct effects and on indications from available scientific studies. These studies include the localization of the receptor, the affinity of ligands with known in vivo activity, and various animal studies conducted so far.

The high levels of receptor found in important structures in the forebrain, including the caudate/putamen, hippocampus, nucleus accumbens, and cortex suggest a role for the receptor in memory and cognition since these areas are known to play a vital role in memory (Gerard, C.; Martres, M.-P.; Lefevre, K.; Miquel, M. C.; Verge, D.; Lanfumey, R.; Doucet, E.; Hamon, M.; E I Mestikawy, S. *Brain Research*, 1997, 746, 207-219). The ability of known 5-HT6 receptor ligands to enhance cholinergic transmission also supported the potential cognition use (Bentley, J. C.; Boursson, A.; Boess, F. G.; Kone, F. C.; Marsden, C. A.; Petit, N.; Sleight, A. J. *British Journal of Pharmacology*, 1999, 126(7), 1537-1542). Studies have found that a known 5-HT6 selective antagonist significantly increased glutamate and aspartate levels in the frontal cortex without elevating levels of noradrenaline, dopamine, or 5-HT. This selective elevation of neurochemicals known to be involved in memory and cognition strongly suggests a role for 5-HT6 ligands in cognition (Dawson, L. A.; Nguyen, H. Q.; Li, P. *British Journal of Pharmacology*, 2000, 130(1), 23-26). Animal studies of memory and learning with a known selective 5-HT6 antagonist found some positive effects (Rogers, D. C.; Hatcher, P. D.; Hagan, J. J. *Society of Neuroscience, Abstracts* 2000, 26, 680). Further support for the role of a selective 5-HT6 ligand in cognition can be found in Woolley, M. L.; Marsden, C. A.; Sleight, A. J.; and Fone, K. C. F., *Psychopharmacology*, 2003, 170(4), 358-367.

A related potential therapeutic use for 5-HT6 ligands is the treatment of attention deficit disorders (ADD, also known as Attention Deficit Hyperactivity Disorder or ADHD) in both children and adults. Because 5-HT6 antagonists appear to enhance the activity of the nigrostriatal dopamine pathway and because ADHD has been linked to abnormalities in the caudate (Ernst, M; Zametkin, A. J.; Matochik, j. H.; Jons, P. A.; Cohen, R. M. *Journal of Neuroscience* 1998, 18(15), 5901-5907), 5-HT6 antagonists may attenuate attention deficit disorders.

Early studies examining the affinity of various CNS ligands with known therapeutic utility or a strong structural resemblance to known drugs suggests a role for 5-HT6 ligands in the treatment of schizophrenia and depression. For example, clozapine (an effective clinical antipsychotic) has high affinity for the 5-HT6 receptor subtype. Also, several clinical antidepressants have high affinity for the receptor as well and act as antagonists at this site (Branchek, T. A.; Blackburn, T. P. *Annual Reviews in Pharmacology and Toxicology* 2000, 40, 319-334).

Further, recent in vivo studies in rats indicate 5-HT6 modulators may be useful in the treatment of movement disorders including epilepsy (Stean, T.; Routledge, C.; Upton, N. *British Journal of Pharmacology* 1999, 127 Proc. Supplement 131P and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M. *British Journal of Pharmacology* 2000, 130(7), 1606-1612).

Taken together, the above studies strongly suggest that compounds which are 5-HT6 receptor modulators, i.e. ligands, may be useful for therapeutic indications including: the treatment of diseases associated with a deficit in memory, cognition, and learning such as Alzheimer's and attention deficit disorder; the treatment of personality disorders such as schizophrenia; the treatment of behavioral disorders, e.g., anxiety, depression and obsessive compulsive disorders; the treatment of motion or motor disorders such as Parkinson's disease and epilepsy; the treatment of diseases associated with neurodegeneration such as stroke and head trauma; or withdrawal from drug addiction including addiction to nicotine, alcohol, and other substances of abuse.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

SUMMARY

The present invention provides a compound of formula I

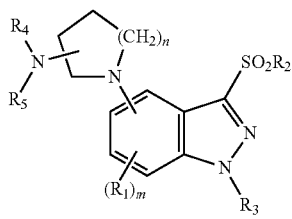

(I)

wherein
- $R_1$ is H, halogen, CN, $COR_9$, $OCO_2R_{10}$, $CO_2R_{11}$, $CONR_{12}R_{13}$, $SO_pR_{14}$, $NR_{15}R_{16}$, $OR_{17}$ or a $C_1$-$C_6$alkyl, $C_3$-$C_7$cycloalkyl, aryl or heteroaryl group each optionally substituted;
- $R_2$ is an optionally substituted aryl, or optionally substituted heteroaryl group or an optionally substituted 8- to 13-membered bicyclic or tricyclic ring system having a N atom at the bridgehead and optionally containing 1, 2 or 3 additional heteroatoms selected from N, O or S;
- $R_3$ is H or $C_1$-$C_6$alkyl or $C_3$-$C_7$cycloalkyl;
- $R_4$ and $R_5$ are each independently H, $C_1$-$C_6$alkyl or $C_3$-$C_7$cycloalkyl or $R_4$ and $R_5$ may be taken together with the atom to which they are attached to form an optionally substituted 3- to 7-membered ring;
- m is an integer of 1, 2 or 3;
- n is 0 or an integer of 1, 2 or 3;
- p is 0 or an integer of 1 or 2;
- $R_9$, $R_{10}$, $R_{11}$ and $R_{17}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
- $R_{12}$, $R_{13}$, $R_{15}$ and $R_{16}$ are each independently H or an optionally substituted $C_1$-$C_4$alkyl group or $R_{12}$ and $R_{13}$ may be taken together with the atom to which they are attached to form a 5- to 7-membered ring optionally containing another heteroatom selected from O, $NR_{18}$ or $SO_p$ or $R_{15}$ and $R_{16}$ may be taken together with the atom to which they are attached to form a 5- to 7-membered ring optionally containing another heteroatom selected from O, $NR_{18}$ or $SO_p$;
- $R_{14}$ is a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted; and
- $R_{18}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteroaryl group each optionally substituted; or a stereoisomer thereof or a pharmaceutically acceptable salt thereof.

The present invention also provides methods and compositions useful in the treatment of central nervous system disorders.

In particular, the present invention provides a pharmaceutical composition, which includes a pharmaceutically acceptable carrier; and at least one compound of formula I.

Another aspect of the present invention provides a method of treatment of a central nervous system disorder related to or affected by the 5-HT6 receptor in a patient in need thereof. The treatment method includes providing the patient with a therapeutically effective amount of a compound of formula I.

A further aspect of the present invention relates to the use of a compound of formula I or a pharmaceutically acceptable salt thereof in the manufacture of a medicament for the treatment of a central nervous system disorder related to or affected by the 5-HT6 receptor in a patient in need thereof.

The present invention further provides a process for the preparation of a compound of formula I, wherein $R_4$ and $R_5$ are each H, which process comprises (i) or (ii) below:

(i) cyclizing a compound of formula (VII):

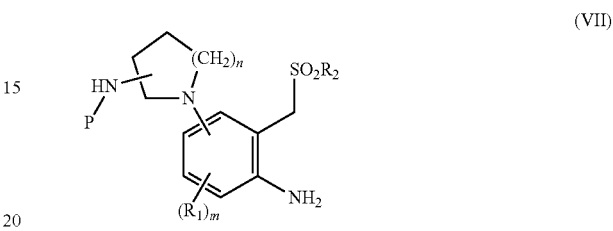

(VII)

wherein, P is a protecting group and $R_1$ and $R_2$ are as defined hereinabove for formula I to form a compound of formula (IX):

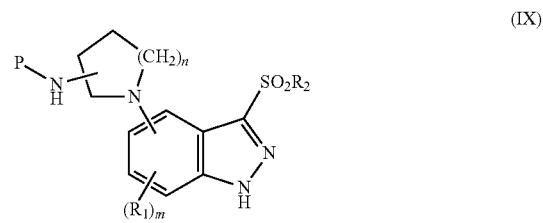

(IX)

and deprotecting said compound of formula (IX) to give the compound of formula (I), wherein $R_3$ of formula I is H;

or (ii) reacting $R_3$-LG with a compound of formula (IX):

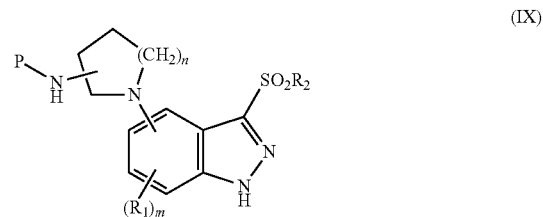

(IX)

wherein $R_3$ is other than H as described hereinabove, LG is a leaving group, P is a protecting group, and $R_1$ and $R_2$ are as defined hereinabove for formula I; and thereafter removing the protecting group to give the compound of formula (I) wherein $R_3$ is other than H as described hereinabove.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders (for example see C. Reavill and D. C. Rogers, Current Opinion in Investigational Drugs, 2001, 2(1):104-109, Pharma Press Ltd.).

Surprisingly, it has now been found that aminoazacyclyl-3-sulfonylindazoles of formula I demonstrate 5-HT6 affinity along with significant 5-HT receptor sub-type selectivity. Advantageously, said formula I indazoles are effective therapeutic agents for the treatment of central nervous system (CNS) disorders associated with or affected by the 5-HT6 receptor. Accordingly, the present invention provides an azacyclyl-3-sulfonylindazole compound of formula I

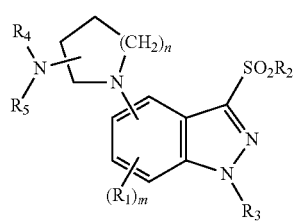

wherein
- $R_1$ is H, halogen, CN, $COR_9$, $OCO_2R_{10}$, $CO_2R_{11}$, $CONR_{12}R_{13}$, $SO_pR_{14}$, $NR_{15}R_{16}$, $OR_{17}$ or a $C_1$-$C_6$alkyl, $C_3$-$C_7$cycloalkyl, aryl or heteroaryl group each optionally substituted;
- $R_2$ is an optionally substituted aryl, or optionally substituted heteroaryl group or an optionally substituted 8- to 13-membered bicyclic or tricyclic ring system having a N atom at the bridgehead and optionally containing 1, 2 or 3 additional heteroatoms selected from N, O or S;
- $R_3$ is H or $C_1$-$C_6$alkyl or $C_3$-$C_7$cycloalkyl;
- $R_4$ and $R_5$ are each independently H, $C_1$-$C_6$alkyl or $C_3$-$C_7$cycloalkyl or $R_4$ and $R_5$ may be taken together with the atom to which they are attached to form an optionally substituted 3- to 7-membered ring;
- m is an integer of 1, 2 or 3;
- n is 0 or an integer of 1, 2 or 3;
- p is 0 or an integer of 1 or 2;
- $R_9$, $R_{10}$, $R_{11}$ and $R_{17}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
- $R_{12}$, $R_{13}$, $R_{15}$ and $R_{16}$ are each independently H or an optionally substituted $C_1$-$C_4$alkyl group or $R_{12}$ and $R_{13}$ may be taken together with the atom to which they are attached to form a 5- to 7-membered ring optionally containing another heteroatom selected from O, $NR_{18}$ or $SO_p$ or $R_{15}$ and $R_{16}$ may be taken together with the atom to which they are attached to form a 5- to 7-membered ring optionally containing another heteroatom selected from O, $NR_{18}$ or $SO_p$;
- $R_{14}$ is a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted; and
- $R_{18}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or hetaryl group each optionally substituted; or a stereoisomer thereof or a pharmaceutically acceptable salt thereof.

It is understood that the claims encompass all possible stereoisomers and prodrugs.

An optionally substituted moiety may be substituted with one or more substituents. The substituent groups, which are optionally present, may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Unless otherwise specified, typically 0-4 substituents may be present. When any of the foregoing substituents represents or contains an alkyl substituent group, this may be linear or branched and may contain up to 12 carbon atoms, preferably up to 6 carbon atoms, more preferably up to 4 carbon atoms.

In another embodiment, the term "optionally substituted" means that the moiety is substituted with 0-4 substituents independently selected from halogen atoms, $C_1$-$C_6$alkyl, $C_1$-$C_6$alkoxy, $C_1$-$C_6$haloalkyl, $C_1$-$C_6$haloalkoxy, $C_1$-$C_6$alkylamino or combinations thereof. In another preferred embodiment, the term "optionally substituted" means that the moiety is substituted with 0-4 substituents independently selected from halogen atoms, $C_1$-$C_6$alkyl, $C_1$-$C_6$alkoxy or combinations thereof. In another more preferred embodiment, the term "optionally substituted" means that the moiety is substituted with 0-4 substituents independently selected from halogen atoms, $C_1$-$C_6$alkyl or combinations thereof.

As used herein, the term "alkyl" includes both a straight chain and a branched chain saturated hydrocarbon moiety. More particularly, "alkyl" refers to monovalent saturated aliphatic hydrocarbyl groups having from 1 to 12 carbon atoms and preferably 1 to 8 carbon atoms ($C_1$-$C_8$ alkyl) and more preferably, 1 to 6 carbon atoms ($C_1$-$C_6$alkyl). Examples of saturated hydrocarbon alkyl moieties, which are $C_1$-$C_6$alkyl groups include, but are not limited to, methyl ($CH_3$—); ethyl ($CH_3CH_2$—); propyl, e.g., n-propyl ($CH_3CH_2CH_2$—) and isopropyl (($CH_3$)$_2$CH—); butyl, e.g., n-butyl ($CH_3CH_2CH_2CH_2$), tert-butyl (($CH_3$)$_3$C—), isobutyl (($CH_3$)$_2$CH$_2$CH$_2$—) and sec-butyl (($CH_3$)($CH_3CH_2$)CH—); pentyl, e.g., n-pentyl ($CH_3CH_2CH_2CH_2CH_2$—) and neopentyl (($CH_3$)$_3$CCH$_2$—); and hexyl groups, e.g., n-hexyl ($CH_3CH_2CH_2CH_2CH_2CH_2$—), or the like. A branched alkyl group has at least 3 carbon atoms (e.g., an isopropyl group), and in various embodiments, has up to 6 carbon atoms. Examples of branched $C_1$-$C_6$alkyl groups include, but are not limited to:

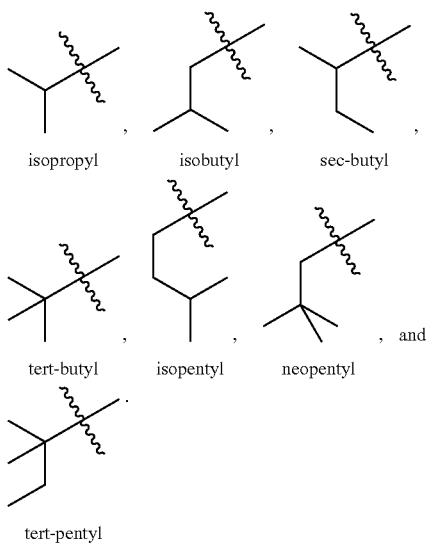

Specifically included within the definition of alkyl are those alkyl groups that are optionally substituted. Suitable alkyl substitutions include, but are not limited to, CN, OH, $NH_2$, halogen, phenyl, carbamoyl, carbonyl, alkoxy or aryloxy.

"Alkenyl", as used herein, refers to alkenyl groups having from 2 to 6 carbon atoms ($C_2$-$C_6$alkenyl) and preferably 2 to 4 carbon atoms ($C_2$-$C_4$alkenyl) and having at least one, and preferably from 1 to 2 sites of alkenyl unsaturation. Such groups are exemplified, for example, by vinyl, allyl, and but-3-en-1-yl.

"Alkynyl" refers to alkynyl groups having from 2 to 6 carbon atoms ($C_2$-$C_6$alkynyl) and preferably 2 to 4 carbon atoms ($C_2$-$C_4$alkynyl) and having at least one, and preferably from 1 to 2 sites of alkynyl unsaturation. Such groups are exemplified by propargyl.

"Amino" refers to the group —$NH_2$.

"Aryl" or "Ar" refers to a monovalent aromatic carbocyclic group of from 6 to 14 carbon atoms having a single (e.g., phenyl) or multiple condensed rings (e.g., naphthyl or anthryl), which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups are $C_6$-$C_{10}$ aryl groups and include phenyl and naphthyl.

"Azacyclic ring" as used herein refers to a ring with the following general structure, wherein n, $R_4$ and $R_5$ are the same as defined for formula I hereinabove:

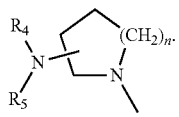

"Cyano" refers to the group —CN.

The term "cycloalkyl", as used herein, refers to a monocyclic, bicyclic, tricyclic, fused, bridged, or spiro monovalent saturated hydrocarbon moiety of 3-7 carbon atoms. Cycloalkyl groups may be saturated or partially saturated. In one embodiment, "cycloalkyl" refers to cyclic alkyl groups of from 3 to 7 carbon atoms having single or multiple cyclic rings including fused, bridged, and spiro ring systems. The term "cycloalkyl" includes bicyclic alkyl groups, and bridged cycloalkyl groups which contain at least one carbon-carbon bond between two non-adjacent carbon atoms of the cycloalkyl ring. Examples of cycloalkyl moieties include, but are not limited to cyclopropyl, cyclobutyl, cyclopentyl, cyclohexyl, cycloheptyl, norbornyl, or the like.

The term "cycloheteroalkyl", as used herein, designates a $C_5$-$C_7$cycloalkyl ring system containing 1, 2 or 3 heteroatoms, which may be the same or different, selected from N, O or S and optionally containing one double bond. Exemplary of the cycloheteroalkyl ring systems included in the term as designated herein are the following rings wherein $X_1$ is NR, O or S and R is H or an optional substituent as defined hereinabove.

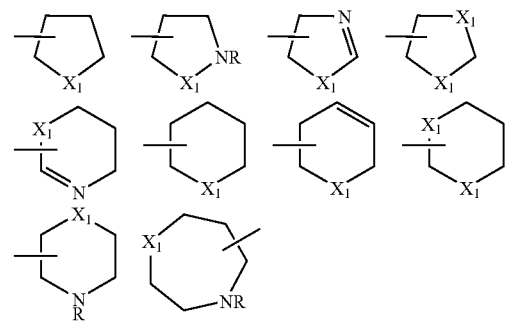

As used herein, the term "haloalkyl" designates a $C_nH_{2n+1}$ group having from one to 2n+1 halogen atoms which may be the same or different. Examples of haloalkyl groups include $CF_3$, $CH_2Cl$, $C_2H_3BrCl$, $C_3H_5F_2$, or the like. A further example of a haloalkyl group is $CHF_2$.

The term "halogen" or "halo", as used herein, designates fluorine, chlorine, bromine, and iodine.

"Hydroxy" or "hydroxyl" refers to the group —OH.

The term "heteroaryl" as used herein designates an aromatic heterocyclic ring system, which may be a single ring (monocyclic) or multiple rings (bicyclic, up to three rings) fused together or linked covalently. Preferably, heteroaryl is a 5- to 6-membered monocyclic ring or a 9- to 10-membered bicyclic ring system. The rings may contain from one to four hetero atoms selected from nitrogen, oxygen, or sulfur, wherein the nitrogen or sulfur atoms are optionally oxidized, or the nitrogen atom is optionally quarternized. Examples of heteroaryl moieties include, but are not limited to, heterocycles such as furan, thiophene, pyrrole, pyrazole, imidazole, oxazole, isoxazole, thiazole, isothiazole, oxadiazole, triazole, pyridine, pyrimidine, pyrazine, pyridazine, benzimidazole, benzoxazole, benzisoxazole, benzothiazole, benzofuran, benzothiophene, thianthrene, dibenzofuran, dibenzothiophene, indole, indazole, quinoline, isoquinoline, quinazoline, quinoxaline, purine, or the like. Preferred heteroaryls include pyridinyl, pyrrolyl, thiophenyl, and furanyl.

"Nitro" refers to the group —$NO_2$.

"Stereoisomer" or "stereoisomers" refer to compounds that differ in the chirality or atomic connectivity at one or more stereocenters. Stereoisomers include enantiomers, diastereomers, as well as cis-trans (E/Z) isomerism.

"Tautomer" refers to alternate forms of a compound that differ in the position of a proton, such as enol-keto and imineenamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

"Patient" or "subject" refers to mammals and includes human and non-human animals, such as dogs, cats, mice, rats, cows, rabbits and monkeys.

"Pharmaceutically acceptable salt" refers to pharmaceutically acceptable salts of a compound, which salts are derived from a variety of organic and inorganic counter ions well known in the art, and include, by way of example only, sodium, potassium, calcium, magnesium, ammonium, and tetraammonium; and when the molecule contains a basic functionality, salts of organic or inorganic acids, such as hydrochloride, hydrobromide, tartrate, mesylate, acetate, maleate, and oxalate. Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

"Treating" or "treatment" of a disease in a subject refers to 1) preventing the disease from occurring in a subject that is predisposed or does not display symptoms of the disease; 2) inhibiting the disease or arresting its development; or 3) ameliorating or causing regression of the disease.

The compounds of the present invention modulate 5-HT6 receptor activity. "Modulating 5-HT6 receptor activity" refers to affecting (i.e., inhibition or potentiation) processes or signaling events associated with the 5-HT6 receptor. Specifically, inhibition of 5-HT6 increases levels of acetylcholine and glutamine in the brain, whereas 5-HT6 receptor agonism or potentiation results in increased cellular cAMP.

A "CNS disease" or "CNS disorder" is a disease or disorder affecting or originating in the central nervous system, preferably a disease related to 5-HT6 activity or affected by 5-HT6 modulation. Particular CNS diseases or disorders include psychoses, anxiety, depression, epilepsy, migraine, cognitive disorders, sleep disorders, feeding disorders, anorexia, bulimia, binge eating disorders, panic attacks, disorders resulting from withdrawal from drug abuse, schizophrenia, gastrointestinal disorders, irritable bowel syndrome, memory disorders, obsessive compulsive disorders, Alzheimer's disease, Parkinson's disease, Huntington's chorea, schizophrenia, attention deficit hyperactive disorder, neurodegenerative diseases characterized by impaired neuronal growth, and pain.

Unless indicated otherwise, the nomenclature of substituents that are not explicitly defined herein are arrived at by naming the terminal portion of the functionality followed by the adjacent functionality toward the point of attachment. For example, the substituent "arylalkyloxycabonyl" refers to the group (aryl)-(alkyl)-O—C(O)—.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of another example, the term "5-7 membered ring" is specifically intended to individually disclose a ring having 5, 6, 7, 5-7, and 5-6 ring atoms.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of formula I, the stereoisomers thereof and the pharmaceutically acceptable salts thereof. The compounds of the invention may be present as a mixture of stereoisomers, individual stereoisomers, or as an optically active or enantiomerically pure form.

Preferred compounds of the invention are those compounds of formula I wherein $R_1$ is H. Another group of preferred compounds are those compounds of formula I wherein $R_2$ is a phenyl or naphthyl group each group optionally substituted. In one preferred embodiment, $R_2$ is an aryl group, such as a phenyl or naphthyl group, optionally substituted by 0-4 substituents independently selected from methyl, ethyl, propyl, isopropyl, chloro, bromo, fluoro, iodo or a combination thereof. A further group of preferred compounds of the invention are those compounds of formula I wherein $R_4$ and $R_5$ are independently H or methyl. Also preferred are those compounds of formula I wherein the azacyclic ring is attached to the indazole in the 5 position.

More preferred compounds of the invention are those compounds of formula I wherein $R_1$ is H; $R_3$ is H or $C_1$ to $C_4$ alkyl; and $R_2$ is a phenyl or naphthyl group each group optionally substituted. Another group of more preferred compounds are those compounds of formula I wherein $R_1$ is H; $R_3$ is H or $C_1$ to $C_4$ alkyl; $R_4$ and $R_5$ are independently H or methyl; $R_2$ is a phenyl or naphthyl group each group optionally substituted; and the azacyclic ring is attached to the indazole in the 5 position. In one preferred embodiment, the optional substituent present in the phenyl or naphthyl group is a $C_1$ to $C_4$ alkyl group or halogen.

Among the preferred compounds of the invention are:
(3R)-1-[3-(1-naphthylsulfonyl)-1H-indazol-5-yl]pyrrolidin-3-amine;
1-[3-(1-naphthylsulfonyl)-1H-indazol-5-yl]piperidin-4-amine;
1-{3-[(4-methyl-1-naphthyl)sulfonyl]-1H-indazol-5-yl}piperidin-4-amine;
1-{3-[(5-chloro-1-naphthyl)sulfonyl]-1H-indazol-5-yl}piperidin-4-amine;
1-{3-[(3-chlorophenyl)sulfonyl]-1H-indazol-5-yl}piperidin-4-amine;
1-[3-(2-naphthylsulfonyl)-1H-indazol-5-yl]piperidin-4-amine;
1-{3-[(4-isopropylphenyl)sulfonyl]-1H-indazol-5-yl}piperidin-4-amine;
1-[3-(1-naphthylsulfonyl)-1H-indazol-5-yl]azetidin-3-amine;
(3S)-1-[3-(1-naphthylsulfonyl)-1H-indazol-5-yl]pyrrolidin-3-amine;
(3S)-1-(3-phenylsulfonyl-1H-indazol-5-yl)pyrrolidin-3-amine;
(3R)-1-(3-phenylsulfonyl-1H-indazol-5-yl)pyrrolidin-3-amine;
(R)—N,N-dimethyl-1-(3-(naphthalen-1-ylsulfonyl)-1H-indazol-5-yl)pyrrolidin-3-amine;
(S)—N,N-dimethyl-1-(3-(naphthalen-1-ylsulfonyl)-1H-indazol-5-yl)pyrrolidin-3-amine;
1-(3-(phenylsulfonyl)-1H-indazol-5-yl)azetidin-3-amine;
(R)-1-(1-methyl-3-(naphthalen-1-ylsulfonyl)-1H-indazol-5-yl)pyrrolidin-3-amine;
(R)-1-(1-isopropyl-3-(naphthalen-1-ylsulfonyl)-1H-indazol-5-yl)pyrrolidin-3-amine;
(R)-1-(1-isobutyl-3-(naphthalen-1-ylsulfonyl)-1H-indazol-5-yl)pyrrolidin-3-amine;
a stereoisomer thereof; or
a pharmaceutically acceptable salt thereof.

In one embodiment, a compound of the present invention exists as a pharmaceutically acceptable salt. More particularly, in one embodiment, the pharmaceutically acceptable salt is hydrochloride (HCl).

Compounds of the invention may be prepared using conventional synthetic methods and, if required, standard separation or isolation techniques. For example, compounds of formula I wherein $R_3$, $R_4$ and $R_5$ are H (Ia) may be prepared by reacting a halonitrobenzene compound of formula II with a chloromethylsulfone of formula III in the presence of strong base, such as KO-t-Bu or KOH, to give the benzylsulfonyl compound of formula IV; reacting said formula IV compound with a protected azacyclylamine of formula V in the presence of a base such as $K_2CO_3$ to give the compound of formula VI; reacting said formula VI compound with a reducing agent such as Sn, Fe or Zn in the presence of an acid or $H_2$ in the presence of a palladium catalyst to give the corresponding amine of formula VII; reacting said amine with $NaNO_2$ in the presence of an acid to give the corresponding protected aminoazacyclyl-3-sulfonylindazole compound; and deprotecting said protected compound to give the desired compound of formula Ia. The reaction is illustrated in flow diagram I wherein Hal represents Cl or F and P represents a protecting group.

FLOW DIAGRAM I

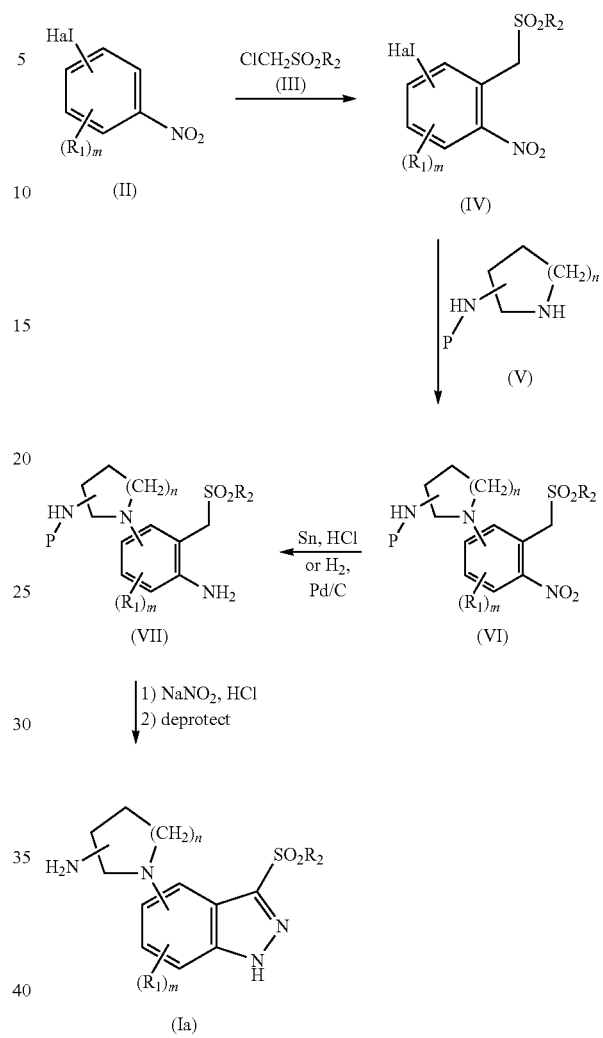

Alternatively, compounds of formula VI may be prepared by reacting a halonitrobenzene compound of formula II with a protected azacyclylamine of formula V in the presence of a base such as $K_2CO_3$ to give the compound of formula VIII and reacting the formula VIII compound with a chloromethylsulfone of formula III in the presence of strong base, such as KO-t-Bu or KOH, to give the desired intermediate compound of formula VI. The reaction is shown in flow diagram II wherein wherein Hal represents Cl or F and P represents a protecting group.

FLOW DIAGRAM II

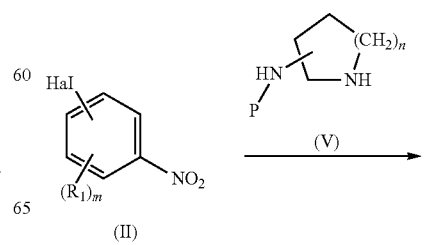

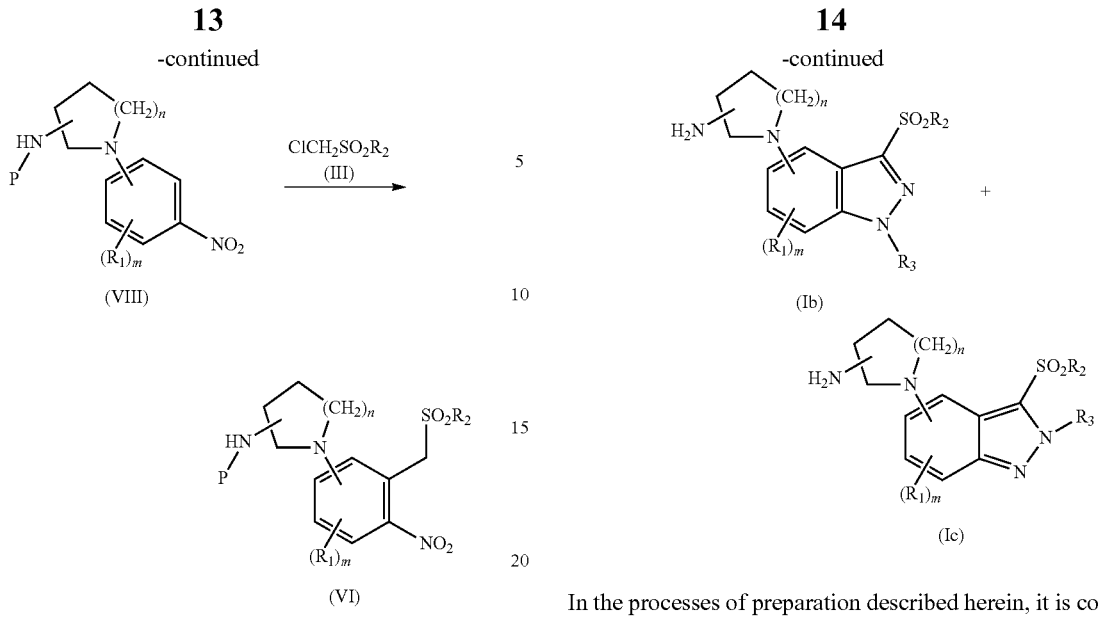

Protecting groups suitable for use in the reactions shown hereinabove include t-butyloxycarbonyl, benzyl, acetyl, benzyloxycarbonyl, or any conventional group known to protect a basic nitrogen in standard synthetic procedures.

The chloromethylarylsulfone reagent (III) used in Flow diagrams I and II was either purchased from commercial resources or prepared via the chemical route depicted below:

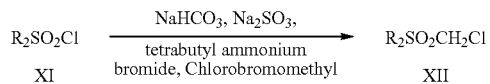

Compounds of formula Ia wherein $R_3$ is other than H and $R_4$ and $R_5$ are H (Ib) may be prepared using conventional alkylation/deprotection procedures. For example, compounds of formula I wherein $R_3$ is other than H and $R_4$ and $R_5$ are H (Ib) may be prepared by reacting a protected compound of formula IX with an alkylating agent of formula X in the presence of a base and a solvent optionally in the presence of a phase-transfer agent to give the corresponding protected alkylated compound and deprotecting said protected compound to give the desired compound of formula Ib. The reaction is shown in flow diagram III wherein P is a protecting group as described hereinabove and LG is a leaving group such as Cl, Br, I, OH, $B(OH)_2$, tosyl, mesyl or the like. Under conditions described in flow diagram III, a byproduct (Ic) from this reaction was isolated and characterized.

FLOW DIAGRAM III

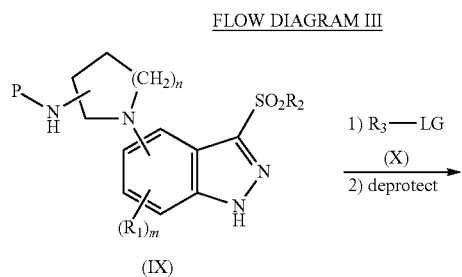

In the processes of preparation described herein, it is contemplated that variables, such as protecting groups, can be modified or substituted in between recited steps, so long as the modified group falls within the claimed genus. For example, in Flow Diagram I, a protecting group P on a compound of formula (VI) may be Cbz, whereas in a later step, the protecting group P at the same position of a compound of formula (VII) may be Boc. In such instances, a 2-step, deprotecting-protecting reaction will occur.

The term "protecting group" with respect to amine groups, hydroxyl groups and sulfhydryl groups refers to forms of these functionalities which are protected from undesirable reaction with a protected group known to those skilled in the art, such as those set forth in Protective Groups in Organic Synthesis, Greene, T. W.; Wuts, P. G. M., John Wiley & Sons, New York, N.Y., ($3^{rd}$ Edition, 1999), the entire disclosure of which is herein incorporated by reference, which protecting groups can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methythiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate. Examples of protected amine groups include, but are not limited to, amides such as, formamide, acetamide, trifluoroacetamide, and benzamide; carbamates; e.g. Boc; imides, such as phthalimide, Fmoc, Cbz, PMB, benzyl, and dithiosuccinimide; and others. Examples of protected or capped sulfhydryl groups include, but are not limited to, thioethers such as S-benzyl thioether, and S-4-picolyl thioether; substituted S-methyl derivatives such as hemithio, dithio and aminothio acetals; and others.

Reference to "leaving group" as used herein indicates having an electrophilic moiety bound to a substituent, capable of being displaced by a nucleophile. Examples of preferred leaving groups are halogens, such as F, Cl, Br or I; triflate; mesylate, or tosylate; esters; aldehydes; ketones; epoxides; and the like. An example of a leaving group is propyliodide, which is readily attacked by a nucleophile, such as a 1-indazolyl group to form a propyl-1-indazolyl functionality.

The terms "deprotecting" or "removing the protecting group" refer to removal of a protecting group, such as removal of a benzyl or BOC group bound to an amine. Deprotecting may be performed by heating and/or addition of reagents capable of removing protecting groups. In preferred embodiments, the deprotecting step involves addition of an acid, base, reducing agent, oxidizing agent, heat, or any combination thereof. One preferred method of removing BOC groups from amino groups is to add HCl or TFA to a solution. Many deprotecting reactions are well known in the art and are described in Protective Groups in Organic Synthesis, Greene, T. W., John Wiley & Sons, New York, N.Y., (1st Edition, 1981), the entire disclosure of which is herein incorporated by reference.

Another aspect of the invention provides a process for the preparation of a compound of formula I:

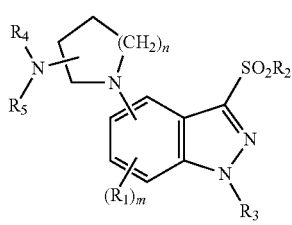

(I)

wherein $R_1$ is H, halogen, CN, $COR_9$, $OCO_2R_{10}$, $CO_2R_{11}$, $CONR_{12}R_{13}$, $SO_pR_{14}$, $NR_{15}R_{16}$, $OR_{17}$ or a $C_1$-$C_6$alkyl, $C_3$-$C_7$cycloalkyl, aryl or heteroaryl group each optionally substituted;

$R_2$ is an optionally substituted aryl, or optionally substituted heteroaryl group or an optionally substituted 8- to 13-membered bicyclic or tricyclic ring system having a N atom at the bridgehead and optionally containing 1, 2 or 3 additional heteroatoms selected from N, O or S;

$R_3$ is H or $C_1$-$C_6$alkyl or $C_3$-$C_7$cycloalkyl;

$R_4$ and $R_5$ are each H;

m is an integer of 1, 2 or 3;

n is 0 or an integer of 1, 2 or 3;

p is 0 or an integer of 1 or 2;

$R_9$, $R_{10}$, $R_{11}$ and $R_{17}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{12}$, $R_{13}$, $R_{15}$ and $R_{16}$ are each independently H or an optionally substituted $C_1$-$C_4$alkyl group or $R_{12}$ and $R_{13}$ may be taken together with the atom to which they are attached to form a 5- to 7-membered ring optionally containing another heteroatom selected from O, $NR_{18}$ or $SO_p$ or $R_{15}$ and $R_{16}$ may be taken together with the atom to which they are attached to form a 5- to 7-membered ring optionally containing another heteroatom selected from O, $NR_{18}$ or $SO_p$;

$R_{14}$ is a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted; and $R_{18}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteraryl group each optionally substituted;

which process comprises (i) or (ii) below:

(i) cyclizing a compound of formula (VII):

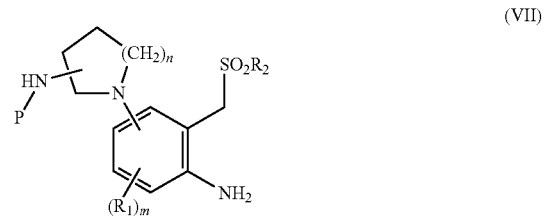

(VII)

wherein, P is a protecting group and $R_1$ and $R_2$ are as defined hereinabove for formula I to form a compound of formula (IX):

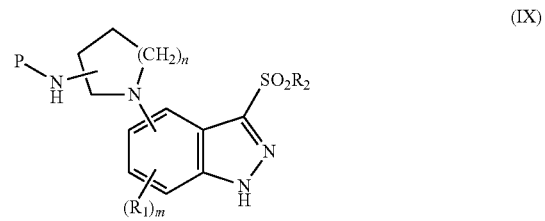

(IX)

and deprotecting said compound of formula (IX) to give the compound of formula (I), wherein $R_3$ of formula I is H;

or (ii) reacting $R_3$-LG with a compound of formula (IX):

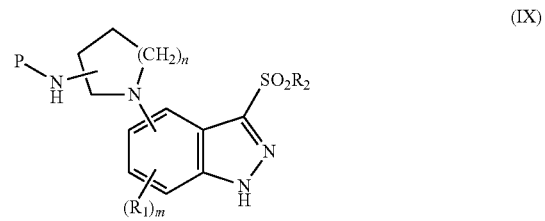

(IX)

wherein $R_3$ is other than H as described hereinabove, LG is a leaving group, P is a protecting group, and $R_1$ and $R_2$ are as defined hereinabove for formula I; and thereafter removing the protecting group to give the compound of formula (I) wherein $R_3$ is other than H as described hereinabove.

In one embodiment, the compound of formula (IX) in (ii) above is prepared by: cyclizing the compound of said formula (VII) to form the compound of formula (IX).

In another embodiment, the cyclizing step includes reacting the compound of formula (VII) with sodium nitrate ($NaNO_2$).

In a further embodiment, the cyclizing step is performed in the presence of HCl.

In some embodiments, the compound of formula (VII) is prepared by: reducing a compound of formula (VI):

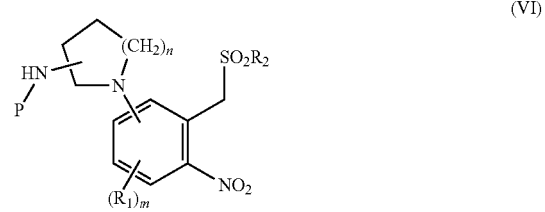

(VI)

wherein, P is a protecting group, and $R_1$ and $R_2$ are as defined hereinabove for formula I, to form the compound of formula (VII).

In one embodiment, the reducing step is performed in the presence of tin chloride ($SnCl_2$) and HCl.

In another embodiment, the reducing step is performed in the presence of $H_2$ and a palladium catalyst.

In one embodiment, the compound of formula (VI) is prepared by: reacting a benzylsulfonyl chloride compound of formula (IV):

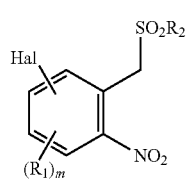

(IV)

wherein, Hal is a halogen atom and $R_1$ and $R_2$ are as defined hereinabove for formula I, with a protected azacyclylamine of formula V:

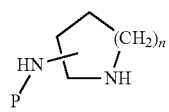

(V)

wherein P is a protecting group,
to form the compound of formula (VI).

In one embodiment, the reacting step is performed in the presence of a base.

The compounds prepared by these processes are useful in vitro or in vivo in modulating 5-HT6 activity. In a particular embodiment, modulating refers to inhibiting activity.

Advantageously, the formula I compounds of the invention are useful for the treatment of CNS disorders relating to or affected by 5-HT6 receptor including motor, mood, personality, behavioral, psychiatric, cognitive, neurodegenerative, or the like disorders, for example Alzheimer's disease, Parkinson's disease, attention deficit disorder, anxiety, epilepsy, depression, obsessive compulsive disorder, sleep disorders, neurodegenerative disorders (such as head trauma or stroke), feeding disorders (such as anorexia or bulimia), schizophrenia, memory loss, disorders associated withdrawal from drug or nicotine abuse, or the like or certain gastrointestinal disorders such as irritable bowel syndrome. Accordingly, the present invention provides a method for the treatment of a disorder of the central nervous system related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The term "providing" as used herein with respect to providing a compound or substance embraced by the invention, designates either directly administering such a compound or substance, or administering a prodrug, derivative or analog which forms an equivalent amount of the compound or substance within the body.

The therapeutically effective amount provided in the treatment of a specific CNS disorder may vary according to the specific condition(s) being treated, the size, age and response pattern of the patient, the severity of the disorder, the judgment of the attending physician or the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Other suitable pharmaceutically acceptable excipients are described in "Remington's Pharmaceutical Sciences," Mack Pub. Co., New Jersey, 1991, incorporated herein by reference.

The compounds of the present invention may be administered to humans and other animals orally, parenterally, sublingually, by aerosolization or inhalation spray, rectally, intracisternally, intravaginally, intraperitoneally, bucally, intrathecally or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Methods of formulation are well known in the art and are disclosed, for example, in Remington: *The Science and Practice of Pharmacy*, Mack Publishing Company, Easton, Pa., 19th Edition (1995). Pharmaceutical compositions for use in the present invention can be in the form of sterile, non-pyrogenic liquid solutions or suspensions, coated capsules, suppositories, lyophilized powders, transdermal patches or other forms known in the art.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-propanediol or 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations may also be prepared by entrapping the drug in liposomes or microemulsions, which are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols)

or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

Compositions of the invention may also be formulated for delivery as a liquid aerosol or inhalable dry powder. Liquid aerosol formulations may be nebulized predominantly into particle sizes that can be delivered to the terminal and respiratory bronchioles.

Effective amounts of the compounds of the invention generally include any amount sufficient to detectably modulate 5-HT6 activity, or by alleviation of symptoms of CNS diseases associated with 5-HT6 activity or susceptible to 5-HT6 activity modulation. The amount of active ingredient that may be combined with the carrier materials to produce a single dosage form will vary depending upon the host treated and the particular mode of administration. It will be understood, however, that the specific dose level for any particular subject will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The term NMR designates proton nuclear magnetic resonance. The terms THF, DMF and DMSO designate tetrahydrofuran, dimethyl formamide and dimethylsulfoxide, respectively. In the chemical drawings, the term Boc represents a t-butoxycarbonyl group.

EXAMPLES

Referring to the examples that follow, compounds of the present invention were synthesized using the methods described herein, or other methods, which are known in the art.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

Example A

General Method for Preparing an Aryl(Het)Chloromethylsulfone

A general method for preparing an aryl(Het)chloromethylsulfone is depicted in the following reaction scheme:

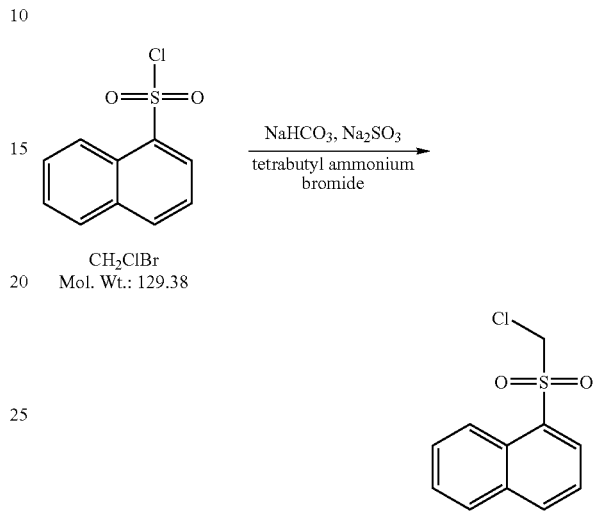

By way of example, 1-naphthylsulfonyl chloride (3.0 g; 13 mmol) was stirred in an aqueous solution (16 mL) of sodium bicarbonate (2.1 g; 25 mmol) and sodium sulfite (3.2 g; 25 mmol) at 100° C. for 1.5 hour. This solution was cooled to room temperature and to it was added the chlorobromomethane (30 g; 232 mmol) and tetrabutylammonium bromide (0.43 g; 1.3 mmol). The mixture was boiled for 18 hours then allowed to cool to room temperature. The volatile components were evaporated and the residue was extracted with dichloromethane, dried over sodium sulfate, filtered and evaporated to obtain a white solid. The white solid was then dissolved in a minimum of dichloromethane and passed through a pad of silica gel. After evaporation, a waxy solid was obtained: 6.64 g, 78%. This material was used in subsequent reaction without further purification.

1H NMR (400 MHz, DMSO-$d_6$) δ ppm 5.36 (s, 2H) 7.67-7.78 (m, 3H) 8.13 (d, J=8.1 Hz, 1H) 8.25 (dd, J=7.36, 1.22 Hz, 1H) 8.37 (d, J=8.23 Hz, 1H) 8.62 (d, J=8.69 Hz, 1H)

Using the procedures described above, other aryl chloromethylsulfones (Table I below) were prepared.

TABLE I

| $R_2SO_2CH_2Cl$ XII | |
|---|---|
| $R_2$ | MS $[M + H]^+$ |
| 4-methylnaphth-1-yl | 255.7 |
| 5-chloronaphth-1-yl | 276.1 |
| 3-chlorophenyl | 226.1 |
| naphth-2-yl | 241.7 |
| 4-isopropylphenyl | 233.7 |
| naphth-1-yl | 241.7 |
| phenyl | 191.7 |

Example 1

Preparation of (3R)-1-[3-(1-Naphthylsulfonyl)-1H-indazol-5-yl]pyrrolidin-3-amine Hydrochloride

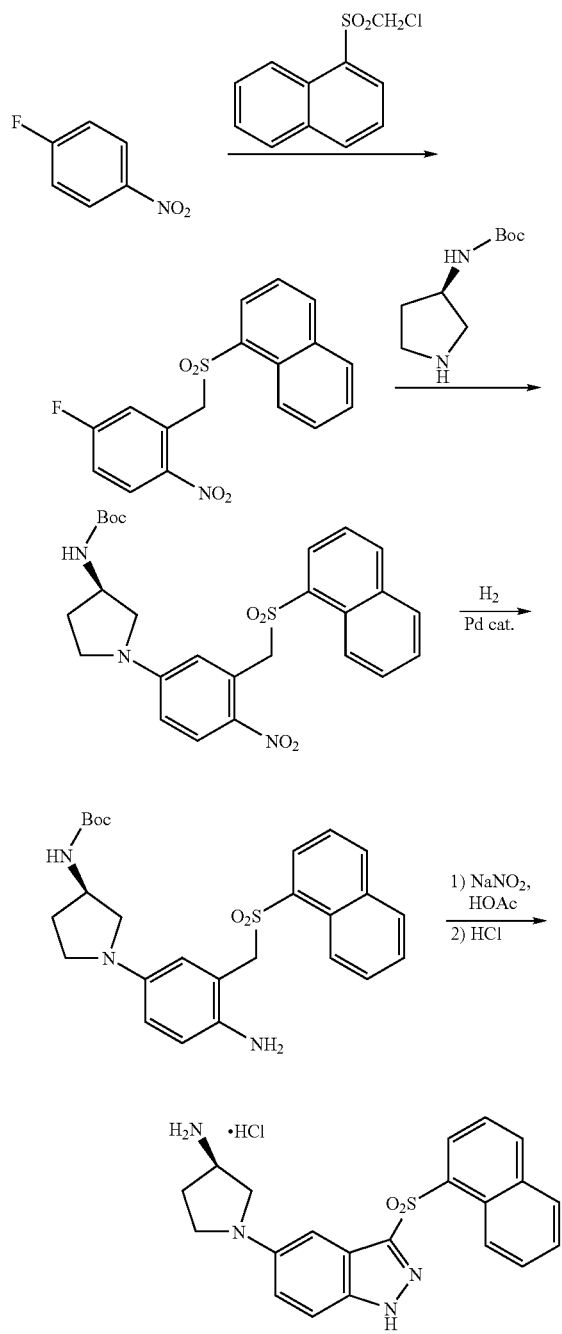

Step 1) Preparation of 1-(5-fluoro-2-nitrobenzylsulfonyl)naphthalene

A stirred solution of 4-fluoro-nitrobenzene (1 equiv.) and chloromethyl-1-naphthylsulfone (1 equiv.) in dry THF under nitrogen at −78° C., was treated with 1.0 M KOt-Bu (2.2 equiv., 1.0 M in THF), warmed to −20° C. over 1 h period, quenched with acetic acid and treated sequentially with water, saturated aqueous NaHCO$_3$ and extracted with ether. The combined extracts were washed with water and brine, dried over MgSO$_4$ and concentrated in vacuo. The resulting residue was chromatographed (Silica gel, 1:1 and 1:0 ethyl acetate: hexanes as eluent) to give 1-(5-fluoro-2-nitrobenzyl-sulfonyl)naphthalene.

Step 2) Preparation of (R)-t-butyl 1-{[3-(naphth-1-ylsulfonyl)methyl]-4-nitrophenyl}pyrrolidin-3-ylcarbamate A stirred solution of (R)-t-butyl pyrrolidin-3-ylcarbamate (1 equiv.), 1-(5-fluoro-2-nitrobenzyl-sulfonyl)naphthalene (1 equiv.), and potassium carbonate (1 equiv.) in ethanol was heated at reflux temperature under nitrogen for 18 h, cooled, diluted with water and extracted with CH$_2$Cl$_2$. The combined extracts were dried over MgSO$_4$ and concentrated in vacuo to give a solid residue. The solid is triturated with 20:80 ethyl acetate:hexanes and filtered. The filtercake was air-dried to afford (R)-t-butyl 1-{[3-(naphth-1-ylsulfonyl)methyl]-4-nitrophenyl}pyrrolidin-3-ylcarbamate.

Step 3) Preparation of (R)-t-butyl 1-{[4-amino-3-(naphth-1-ylsulfonyl)methyl]-phenyl}pyrrolidin-3-ylcarbamate A solution of (R)-t-butyl 1-{[3-(naphth-1-ylsulfonyl)methyl]-4-nitrophenyl}pyrrolidin-3-ylcarbamate (1.0 equiv.) in ethanol was treated with 10% Pd on carbon (0.1 equiv.). The mixture was hydrogenated in a Parr flask at 50 psi overnight. The reaction mixture was filtered over celite and the filtrate was evaporated in vacuo to give (R)-t-butyl 1-{[4-amino-3-(naphth-1-ylsulfonyl)methyl]phenyl}pyrrolidin-3-ylcarbamate.

Step 4) Preparation of (3R)-1-[3-(1-Naphthylsulfonyl)-1H-indazol-5-yl]pyrrolidin-3-amine Hydrochloride A stirred solution of (R)-t-butyl 1-{[4-amino-3-(naphth-1-ylsulfonyl)methyl]-phenyl}pyrrolidin-3-ylcarbamate (1 equiv.) in acetic acid was treated with an aqueous solution of sodium nitrite (1.5 equiv.). The acetic acid was evaporated and the residue was dissolved in dichloromethane, washed with dilute aqueous sodium bicarbonate, dried over magnesium sulfate, filtered and evaporated. The residue was chromatographed on silica gel eluted with dichloromethane and methanol to give (R)-t-butyl 1-[(3-(nathth-1-ylsulfonyl)-1H-indazol-5-yl]pyrrolidin-3-ylcarbamate.

A portion of (R)-t-butyl 1-[(3-(nathth-1-ylsulfonyl)-1H-indazol-5-yl]pyrrolidin-3-ylcarbamate was dissolved in a mixture of ethanol and CH$_2$Cl$_2$, treated with 4.0 M HCl in dioxane and concentrated in vacuo to give a solid residue. The residue was triturated with ethyl acetate and filtered. The filter cake was dried to afford the title product as a green solid, identified by NMR and mass spectral analyses.

1H NMR (400 MHz, DMSO-d$_6$) δ ppm 2.06-2.19 (m, J=4.9 Hz, 1H) 2.28-2.42 (m, 1H) 3.27-3.41 (m, 2H) 3.49-3.61 (m, 2H) 3.96 (br. s., 1H) 6.77 (d, J=2.0 Hz, 1H) 6.97 (dd, J=9.0, 2.2 Hz, 1H) 7.52 (d, J=9.0 Hz, 1H) 7.56-7.68 (m, 2H) 7.76 (dd, J=7.8 Hz, 1H) 8.03-8.10 (m, 1H) 8.25-8.37 (m, 3H)

8.52 (dd, J=7.3, 1.2 Hz, 1H) 8.80 (d, j=8.8 Hz, 1H) 14.02 (br. s., 1H). MS (ES) m/z 393.1; MS (ES) m/z 785.3;

Example 2

Preparation of 1-[3-(1-naphthylsulfonyl)-1H-indazol-5-yl]piperidin-4-amine Hydrochloride

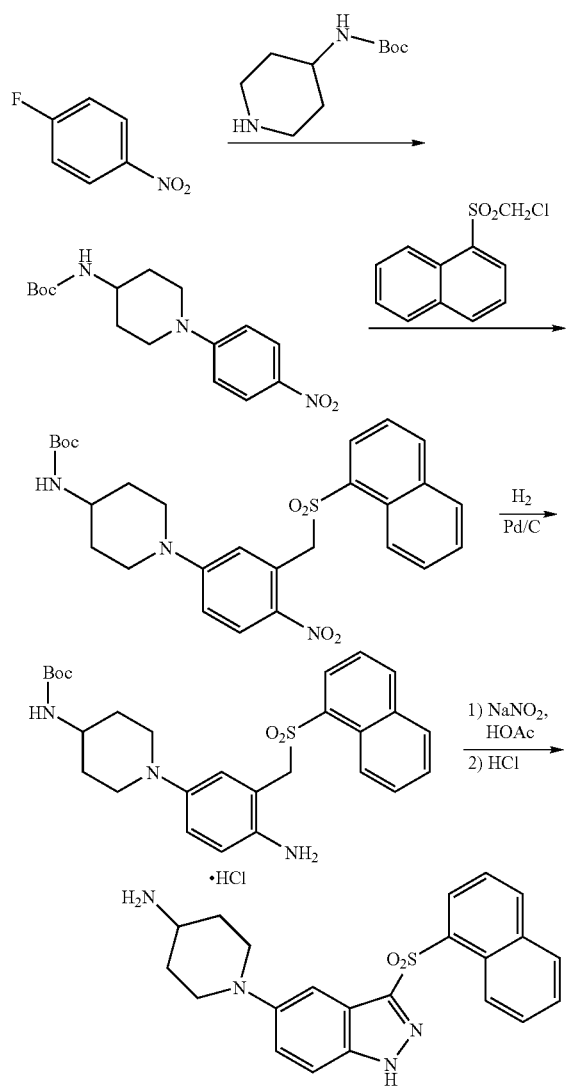

Step 1) Preparation of t-butyl 1-(4-nitrophenyl)piperidin-4-ylcarbamate

A stirred solution of the t-butyl piperidin-4-ylcarbamate (1 equiv.), 4-fluoronitrobenzene (1 equiv.), and potassium carbonate (1 equiv.) in ethanol was heated at reflux temperature under nitrogen for 18 h, cooled, diluted with water and extracted with CH$_2$Cl$_2$. The combined extracts were dried over MgSO$_4$ and concentrated in vacuo to give a solid residue. The solid was triturated with 20:80 ethyl acetate:hexanes and filtered. The filtercake was air-dried to afford t-butyl 1-(4-nitrophenyl)piperidin-4-ylcarbamate.

Step 2) Preparation of t-butyl 1-{3-[(naphth-1-ylsulfonyl)methyl]-4-nitrophenyl}-piperidin-4-ylcarbamate A stirred solution of (1 equiv.) and chloromethyl-1-naphthylsulfone (1 equiv.) in dry THF under nitrogen at −78° C., was treated with 1.0 M KOt-Bu in THF (2.2 equiv.), warmed to −20° C. over 1 h period, quenched with acetic acid and treated sequentially with water, saturated aqueous NaHCO$_3$ and extracted with ether. The combined extracts were washed with water and brine, dried over MgSO$_4$ and concentrated in vacuo. The resulting residue was chromatographed (Silica gel, 1:1 and 1:0 ethyl acetate:hexanes as eluent) to give 1-(5-fluoro-2-nitrobenzyl-sulfonyl)naphthalene.

Steps 3 and 4) Preparation of 1-[3-(1-naphthylsulfonyl)-1H-indazol-5-yl]piperidin-4-amine Hydrochloride Using essentially the same procedure described in Example 1, Steps 3 and 4, and employing 1-(5-fluoro-2-nitrobenzyl-sulfonyl)naphthalene as starting material, the title product was obtained as a light tan powder, identified by NMR and mass spectral analyses. 1H NMR (400 MHz, DMSO-d$_6$) δ ppm 1.96-2.15 (m, 2H) 2.22 (d, J=11.0 Hz, 2H) 3.23-3.50 (m, 2H) 3.73 (d, J=11.5 Hz, 2H) 3.88 (s, 3H) 7.58-7.64 (m, 1H) 7.65-7.71 (m, 1H) 7.71-7.81 (m, 3H) 8.07 (d, J=7.8 Hz, 2H) 8.31 (d, J=8.3 Hz, 1H) 8.47 (s, 2H) 8.60 (dd, J=7.3, 1.0 Hz, 1H) 8.81 (d, J=8.5 Hz, 1H) 14.53 (s, 1H). MS (ES) m/z 407.1;

Examples 3-14

Preparation of 5-(Aminoazacyclyl)-3-arylsulfonyl-1H-indazole Hydrochloride Derivatives Using essentially the same procedures described in Examples 1 and 2 hereinabove and employing the appropriate chloromethylarylsulfone and the desired Boc-protected azacyclylamine reagent, the compounds shown in Table II, wherein R$_3$ is H (Examples 3-14) were obtained and identified by HNMR and mass spectral analyses.

TABLE II

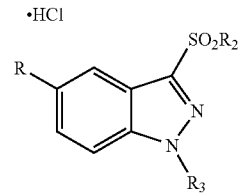

| Ex No | R | R$_3$ | R$_2$ | MS [M + H]$^+$ |
|---|---|---|---|---|
| 3 | 1-piperidin-4-amine | H | 4-methylnaphth-1-yl | 419.2 |
| 4 | 1-piperidin-4-amine | H | 5-chloronaphth-1-yl | 439.0 |
| 5 | 1-piperidin-4-amine | H | 3-chlorophenyl | 391.0 |
| 6 | 1-piperidin-4-amine | H | naphth-2-yl | 405.1 |
| 7 | 1-piperidin-4-amine | H | 4-isopropylphenyl | 397.2 |
| 8 | 1-azetidin-3-amine | H | naphth-1-yl | 379.1 |
| 9 | 3-(S)-1-pyrrolidin-3-amine | H | naphth-1-yl | 393.1 |
| 10 | 3-(S)-1-pyrrolidin-3-amine | H | phenyl | 343.1 |
| 11 | 3-(R)-1-pyrrolidin-3-amine | H | phenyl | 343.1 |
| 12 | 3-(R)-1-pyrrolidin-3-dimethylamine | H | naphth-1-yl | 421.1 |

TABLE II-continued

·HCl

R—[indazole with SO₂R₂ at 3-position, R₃ at N1]

| Ex No | R | R₃ | R₂ | MS [M + H]⁺ |
|---|---|---|---|---|
| 13 | 3-(S)-1-pyrrolidin-3-dimethylamine | H | naphth-1-yl | 421.1 |
| 14 | 1-azetidin-3-amine | H | phenyl | 329.0 |
| 15 | 3-(R)-1-pyrrolidin-3-amine | Me | naphth-1-yl | 407.1 |
| 16 | 3-(R)-1-pyrrolidin-3-amine | i-Pr | naphth-1-yl | 435.2 |
| 17 | 3-(R)-1-pyrrolidin-3-amine | i-Bu | naphth-1-yl | 449.2 |

Example 15

Preparation of (3R)-1-[1-methyl-3-(naphthalen-1-ylsulfonyl)-1H-indazol-5-yl]pyrrolidin-3-amine Using the chemical synthesis route depicted below, which essentially corresponds to Flow Diagram III in the description section, the title compound of Example 15 in Table II above was formed, along with a byproduct of the reaction (an isomer alkylated at N-2), which was isolated and characterized (Example 18 in Table III).

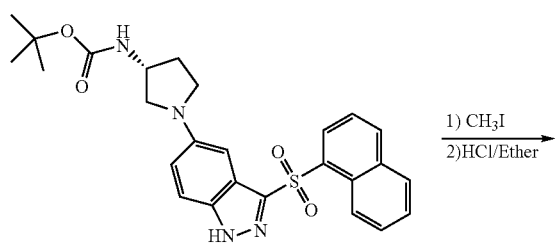

1) CH₃I
2) HCl/Ether

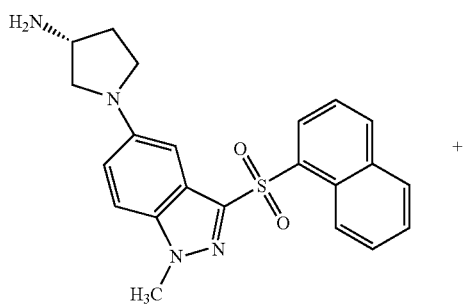

15

+

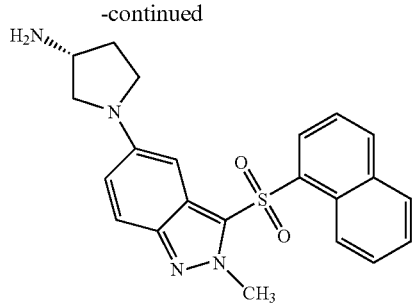

18

Step 1) Preparation of Tert-butyl {(3R)-1-[1-methyl-3-(naphthalen-1-ylsulfonyl)-1H-indazol-5-yl]pyrrolidin-3-yl}carbamate and tert-butyl {(3R)-1-[2-methyl-3-(naphthalen-1-ylsulfonyl)-2H-indazol-5-yl]pyrrolidin-3-yl}carbamate To an N,N-dimethylformamide solution of tert-butyl {(3R)-1-[3-(1-naphthylsulfonyl)-1H-indazol-5-yl]pyrrolidin-3-yl}carbamate (0.300 g, 0.609 mmol) was added cesium carbonate (0.198 g, 0.609 mmol). After 10 min, methyl iodide (0.046 mL, 0.104 mmol) was added and the reaction mixture was stirred for one hour. The reaction mixture was quenched with water, extracted with ethyl acetate (three times), dried over magnesium sulfate, concentrated and purified by column chromatography to afford tert-butyl {(3R)-1-[1-methyl-3-(naphthalen-1-ylsulfonyl)-1H-indazol-5-yl]pyrrolidin-3-yl}carbamate (223 mg, 72%) and tert-butyl {(3R)-1-[2-methyl-3-(naphthalen-1-ylsulfonyl)-2H-indazol-5-yl]pyrrolidin-3-yl}carbamate (53 mg, 17%)

Step 2) Preparation of (3R)-1-[1-methyl-3-(naphthalen-1-ylsulfonyl)-1H-indazol-5-yl]pyrrolidin-3-amine (Example 15)

tert-Butyl {(3R)-1-[1-methyl-3-(naphthalen-1-ylsulfonyl)-1H-indazol-5-yl]pyrrolidin-3-yl}carbamate (0.200 g, 0.395 mmol) was dissolved in dichloromethane and to this was added trifluoroacetic acid (1 mL). The reaction mixture was stirred at room temperature over night. The solvent and excess trifluoroacetic acid was evaporated and the residue was dissolved in ethyl acetate. The organic mixture was washed with saturated aqueous potassium carbonate. The solvent was evaporated to afford a pure (3R)-1-[1-methyl-3-(naphthalen-1-ylsulfonyl)-1H-indazol-5-yl]pyrrolidin-3-amine (15, 0.147 g, 92%).

Examples 16 and 17

Using conditions similar to those described for example 15, two additional examples, examples 16 and 17 (Table II, above) were prepared. In each case, an isomer (alkylated at N-2) was isolated and characterized (Table III). The alkylated isomers formed as byproducts during the preparation of Examples 16 and 17 correspond to compounds 19 and 20, respectively, in Table III below.

TABLE III

[Chemical structure: naphthalene-SO2 group attached to indazole core with pyrrolidine substituent bearing H2N group, and N-R3]

| Compound | R₃ | MS [M + H]⁺ |
|---|---|---|
| 18 | Me | 407.1 |
| 19 | i-Pr | 435.2 |
| 20 | i-Bu | 449.2 |

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10-25 μl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 μl. To each well is added the following mixture: 80.0 μl of incubation buffer made in 50 mM Tris.HCl buffer (pH 7.4) containing 10.0 mM $MgCl_2$ and 0.5 mM EDTA and 20 μl of [$^3$H]-LSD (S.A., 86.0 Ci/mmol, available from Amersham Life Science), 3.0 nM. The dissociation constant, $K_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 μl of tissue suspension. Nonspecific binding is measured in the presence of 10.0 μM methiothepin. The test compounds are added in 20.0 μl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 μl Microscint®-20 scintillant to each shallow well. The unifilter plate is heat-sealed and counted in a PackardTopCount® with a tritium efficiency of 31.0%.

Specific binding to the 5-HT6 receptor is defined as the total radioactivity bound less the amount bound in the presence of 10.0 μM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yields both the $IC_{50}$ and the $K_i$ values of test compounds with 95% confidence limits.

Alternatively, a linear regression line of data points is plotted, from which the $IC_{50}$ value is determined and the $K_i$ value is determined based upon the following equation:

$$K_i = IC_{50}/(1+L/K_D)$$

where L is the concentration of the radioactive ligand used and $K_D$ is the dissociation constant of the ligand for the receptor, both expressed in nM.

Using this assay, the Ki values are determined and compared to those values obtained by representative compounds known to demonstrate binding to the 5-HT6 receptor. The data are shown in Table IV, below.

TABLE IV

| Ex. No. | 5-HT6 Binding Ki (nM) |
|---|---|
| 1 | 4.5 |
| 2 | 4.3 |
| 3 | 3.6 |
| 4 | 4.5 |
| 5 | 8.0 |
| 6 | 18.2 |
| 7 | 13.1 |
| 8 | 3.5 |
| 9 | 3.0 |
| 10 | 131 |
| 11 | 146 |
| 12 | 1.1 |
| 13 | 50 |
| 14 | 1.1 |
| 15 | 21.1 |
| 16 | 13.7 |
| 17 | 36.9 |
| 18 | 54.3 |
| 19 | 48.7 |
| 20 | 75.8 |
| Comparative Examples | |
| Clozapine | 6.0 |
| Loxapine | 41.4 |
| Bromocriptine | 23.0 |
| Methiothepin | 8.3 |
| Mianserin | 44.2 |
| Olanzepine | 19.5 |

What is claimed is:

1. A compound of formula I

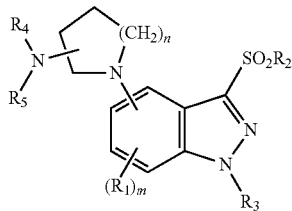

wherein
R$_1$ is H, halogen, CN, COR$_9$, OCO$_2$R$_{10}$, CO$_2$R$_{11}$, CONR$_{12}$R$_{13}$, SO$_p$R$_{14}$, NR$_{15}$R$_{16}$, OR$_{17}$ or a C$_1$-C$_6$alkyl, C$_3$-C$_7$cycloalkyl, aryl or heteroaryl group each optionally substituted;
R$_2$ is an optionally substituted aryl, or optionally substituted heteroaryl group or an optionally substituted 8- to 13-membered bicyclic or tricyclic ring system having a N atom at the bridgehead and optionally containing 1, 2 or 3 additional heteroatoms selected from N, O or S;
R$_3$ is H, C$_1$-C$_6$alkyl or C$_3$-C$_7$cycloalkyl;
R$_4$ and R$_5$ are each independently H, C$_1$-C$_6$alkyl or C$_3$-C$_7$cycloalkyl or R$_4$ and R$_5$ may be taken together with the atom to which they are attached to form an optionally substituted 3- to 7-membered ring;
m is an integer of 1, 2 or 3;
n is 0 or an integer of 1, 2 or 3;
p is 0 or an integer of 1 or 2;
R$_9$, R$_{10}$, R$_{11}$, and R$_{17}$ are each independently H or a C$_1$-C$_6$alkyl, C$_2$-C$_6$alkenyl, C$_2$-C$_6$alkynyl, C$_3$-C$_6$cycloalkyl, cycloheteroalkyl, aryl or heteroaryl group each optionally substituted;
R$_{12}$, R$_{13}$, R$_{15}$ and R$_{16}$ are each independently H or an optionally substituted C$_1$-C$_4$alkyl group or R$_{12}$ and R$_{13}$ may be taken together with the atom to which they are attached to form a 5- to 7-membered ring optionally containing another heteroatom selected from O, NR$_{18}$ or SO$_p$ or R$_{15}$ and R$_{16}$ may be taken together with the atom to which they are attached to form a 5- to 7-membered ring optionally containing another heteroatom selected from O, NR$_{18}$ or SO$_p$;
R$_{14}$ is a C$_1$-C$_6$alkyl, C$_2$-C$_6$alkenyl, C$_2$-C$_6$alkynyl, C$_3$-C$_6$cycloalkyl, cycloheteroalkyl, aryl or heteroaryl group each optionally substituted; and
R$_{18}$ is H or a C$_1$-C$_6$alkyl, C$_2$-C$_6$alkenyl, C$_2$-C$_6$alkynyl, C$_3$-C$_7$cycloalkyl, cycloheteroalkyl, aryl or heteraryl group each optionally substituted; or
a stereoisomer thereof or a pharmaceutically acceptable salt thereof.

2. The compound according to claim 1 wherein R$_1$ is H.

3. The compound according to claim 1 wherein R$_2$ is an optionally substituted phenyl or naphthyl group.

4. The compound according to claim 3 wherein the optional substituent present in the phenyl or naphthyl group is a C$_1$ to C$_4$ alkyl group or halogen.

5. The compound according to claim 1 wherein R$_3$ is H or C$_1$ to C$_4$alkyl.

6. The compound according to claim 1 wherein the azacyclic ring is attached to the indazole in the 5 position.

7. The compound according to claim 2 wherein R$_4$ and R$_5$ are independently H or methyl.

8. The compound according to claim 6 wherein R$_2$ is an optionally substituted phenyl or naphthyl group.

9. The compound according to claim 1 in which the azacyclic ring is a 1-piperidin-4-amine, a 1-azetidine-3-amine or a 1-pyrrolidin-3-amine.

10. The compound according to claim 1 selected from the group consisting of:
(3R)-1-[3-(1-naphthylsulfonyl)-1H-indazol-5-yl]pyrrolidin-3-amine;
1-[3-(1-naphthylsulfonyl)-1H-indazol-5-yl]piperidin-4-amine;
1-{3-[(4-methyl-1-naphthyl)sulfonyl]-1H-indazol-5-yl}piperidin-4-amine;
1-{3-[(5-chloro-1-naphthyl)sulfonyl]-1H-indazol-5-yl}piperidin-4-amine;
1-{3-[(3-chlorophenyl)sulfonyl]-1H-indazol-5-yl}piperidin-4-amine;
1-[3-(2-naphthylsulfonyl)-1H-indazol-5-yl]piperidin-4-amine;
1-{3-[(4-isopropylphenyl)sulfonyl]-1H-indazol-5-yl}piperidin-4-amine;
1-[3-(1-naphthylsulfonyl)-1H-indazol-5-yl]azetidin-3-amine;
(3S)-1-[3-(1-naphthylsulfonyl)-1H-indazol-5-yl]pyrrolidin-3-amine;
(3S)-1-(3-phenylsulfonyl-1H-indazol-5-yl)pyrrolidin-3-amine;
(3R)-1-(3-phenylsulfonyl-1H-indazol-5-yl)pyrrolidin-3-amine;
(R)—N,N-dimethyl-1-(3-(naphthalen-1-ylsulfonyl)-1H-indazol-5-yl)pyrrolidin-3-amine;
(S)—N,N-dimethyl-1-(3-(naphthalen-1-ylsulfonyl)-1H-indazol-5-yl)pyrrolidin-3-amine;
1-(3-(phenylsulfonyl)-1H-indazol-5-yl)azetidin-3-amine;
(R)-1-(1-methyl-3-(naphthalen-1-ylsulfonyl)-1H-indazol-5-yl)pyrrolidin-3-amine;
(R)-1-(1-isopropyl-3-(naphthalen-1-ylsulfonyl)-1H-indazol-5-yl)pyrrolidin-3-amine;
(R)-1-(1-isobutyl-3-(naphthalen-1-ylsulfonyl)-1H-indazol-5-yl)pyrrolidin-3-amine;
a stereoisomer thereof; and
a pharmaceutically acceptable salt thereof.

11. A method for the treatment of a central nervous system disorder related to or affected by the 5-HT6 receptor in a patient in need thereof which comprises providing to said patient a therapeutically effective amount of a compound of formula I

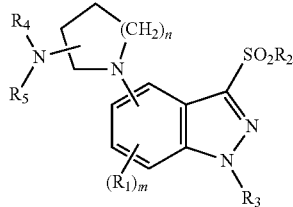

wherein
R$_1$ is H, halogen, CN, COR$_9$, OCO$_2$R$_{10}$, CO$_2$R$_{11}$, CONR$_{12}$R$_{13}$, SO$_p$R$_{14}$, NR$_{15}$R$_{16}$, OR$_{17}$ or a C$_1$-C$_6$alkyl, C$_3$-C$_7$cycloalkyl, aryl or heteroaryl group each optionally substituted;
R$_2$ is an optionally substituted aryl, or optionally substituted heteroaryl group or an optionally substituted 8- to 13-membered bicyclic or tricyclic ring system having a N atom at the bridgehead and optionally containing 1, 2 or 3 additional heteroatoms selected from N, O or S;

$R_3$ is H or $C_1$-$C_6$alkyl or $C_3$-$C_7$cycloalkyl;

$R_4$ and $R_5$ are each independently H, $C_1$-$C_6$alkyl or $C_3$-$C_7$cycloalkyl or $R_4$ and $R_5$ may be taken together with the atom to which they are attached to form an optionally substituted 3- to 7-membered ring;

m is an integer of 1, 2 or 3;

n is 0 or an integer of 1, 2 or 3;

p is 0 or an integer of 1 or 2;

$R_9$, $R_{10}$, $R_{11}$ and $R_{17}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{12}$, $R_{13}$, $R_{15}$ and $R_{16}$ are each independently H or an optionally substituted $C_1$-$C_4$alkyl group or $R_{12}$ and $R_{13}$ may be taken together with the atom to which they are attached to form a 5- to 7-membered ring optionally containing another heteroatom selected from O, $NR_{18}$ or $SO_p$ or $R_{15}$ and $R_{16}$ may be taken together with the atom to which they are attached to form a 5- to 7-membered ring optionally containing another heteroatom selected from O, $NR_{18}$ or $SO_p$;

$R_{14}$ is a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted; and $R_{18}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteraryl group each optionally substituted; or a stereoisomer thereof or a pharmaceutically acceptable salt thereof.

12. The method according to claim 11 wherein said disorder is selected from the group consisting of: attention deficit disorder; obsessive compulsive disorder; withdrawal from drug, alcohol or nicotine addiction; schizophrenia; depression; and Alzheimer's disease.

13. A pharmaceutical composition which comprises a pharmaceutically acceptable carrier and at least one compound of formula I $$\text{(I)}$$

wherein $R_1$ is H, halogen, CN, $COR_9$, $OCO_2R_{10}$, $CO_2R_{11}$, $CONR_{12}R_{13}$, $SO_pR_{14}$, $NR_{15}R_{16}$, $OR_{17}$ or a $C_1$-$C_6$alkyl, $C_3$-$C_7$cycloalkyl, aryl or heteroaryl group each optionally substituted;

$R_2$ is an optionally substituted aryl, or optionally substituted heteroaryl group or an optionally substituted 8- to 13-membered bicyclic or tricyclic ring system having a N atom at the bridgehead and optionally containing 1, 2 or 3 additional heteroatoms selected from N, O or S;

$R_3$ is H or $C_1$-$C_6$alkyl or $C_3$-$C_7$cycloalkyl;

$R_4$ and $R_5$ are each independently H, $C_1$-$C_6$alkyl or $C_3$-$C_7$cycloalkyl or $R_4$ and $R_5$ may be taken together with the atom to which they are attached to form an optionally substituted 3- to 7-membered ring;

m is an integer of 1, 2 or 3;

n is 0 or an integer of 1, 2 or 3;

p is 0 or an integer of 1 or 2;

$R_9$, $R_{10}$, $R_{11}$, and $R_{17}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{12}$, $R_{13}$, $R_{15}$ and $R_{16}$ are each independently H or an optionally substituted $C_1$-$C_4$alkyl group or $R_{12}$ and $R_{13}$ may be taken together with the atom to which they are attached to form a 5- to 7-membered ring optionally containing another heteroatom selected from O, $NR_{18}$ or $SO_p$ or $R_{15}$ and $R_{16}$ may be taken together with the atom to which they are attached to form a 5- to 7-membered ring optionally containing another heteroatom selected from O, $NR_{18}$ or $SO_p$;

$R_{14}$ is a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted; and $R_{18}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteraryl group each optionally substituted; or a stereoisomer thereof or a pharmaceutically acceptable salt thereof.

14. The composition according to claim 13 having a formula I compound wherein $R_1$ is H.

15. The composition according to claim 14 having a formula I compound wherein $R_2$ is a phenyl or naphthyl group each group optionally substituted.

16. The composition according to claim 15 having a formula I compound wherein $R_3$ is H or $C_1$ to $C_4$alkyl; and $R_4$ and $R_5$ are independently H or methyl.

17. The composition according to claim 16 having a formula I compound wherein the azacyclic ring is attached to the indazole in the 5 position.

18. The composition according to claim 13 having a formula I compound selected from the group consisting of:

(3R)-1-[3-(1-naphthylsulfonyl)-1H-indazol-5-yl]pyrrolidin-3-amine;

1-[3-(1-naphthylsulfonyl)-1H-indazol-5-yl]piperidin-4-amine;

1-{3-[(4-methyl-1-naphthyl)sulfonyl]-1H-indazol-5-yl}piperidin-4-amine;

1-{3-[(5-chloro-1-naphthyl)sulfonyl]-1H-indazol-5-yl}piperidin-4-amine;

1-{3-[(3-chlorophenyl)sulfonyl]-1H-indazol-5-yl}piperidin-4-amine;

1-[3-(2-naphthylsulfonyl)-1H-indazol-5-yl]piperidin-4-amine;

1-{3-[(4-isopropylphenyl)sulfonyl]-1H-indazol-5-yl}piperidin-4-amine;

1-[3-(1-naphthylsulfonyl)-1H-indazol-5-yl]azetidin-3-amine;

(3S)-1-[3-(1-naphthylsulfonyl)-1H-indazol-5-yl]pyrrolidin-3-amine;

(3S)-1-(3-phenylsulfonyl-1H-indazol-5-yl)pyrrolidin-3-amine;

(3R)-1-(3-phenylsulfonyl-1H-indazol-5-yl)pyrrolidin-3-amine;

(R)—N,N-dimethyl-1-(3-(naphthalen-1-ylsulfonyl)-1H-indazol-5-yl)pyrrolidin-3-amine;

(S)—N,N-dimethyl-1-(3-(naphthalen-1-ylsulfonyl)-1H-indazol-5-yl)pyrrolidin-3-amine;

1-(3-(phenylsulfonyl)-1H-indazol-5-yl)azetidin-3-amine;

(R)-1-(1-methyl-3-(naphthalen-1-ylsulfonyl)-1H-indazol-5-yl)pyrrolidin-3-amine;

(R)-1-(1-isopropyl-3-(naphthalen-1-ylsulfonyl)-1H-indazol-5-yl)pyrrolidin-3-amine;

(R)-1-(1-isobutyl-3-(naphthalen-1-ylsulfonyl)-1H-indazol-5-yl)pyrrolidin-3-amine;

a stereoisomer thereof; and a pharmaceutically acceptable salt thereof.

19. A process for the preparation of a compound of formula I:

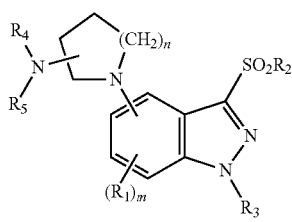

(I)

wherein $R_1$ is H, halogen, CN, $COR_9$, $OCO_2R_{10}$, $CO_2R_{11}$, $CONR_{12}R_{13}$, $SO_pR_{14}$, $NR_{15}R_{16}$, $OR_{17}$ or a $C_1$-$C_6$alkyl, $C_3$-$C_7$cycloalkyl, aryl or heteroaryl group each optionally substituted;

$R_2$ is an optionally substituted aryl, or optionally substituted heteroaryl group or an optionally substituted 8- to 13-membered bicyclic or tricyclic ring system having a N atom at the bridgehead and optionally containing 1, 2 or 3 additional heteroatoms selected from N, O or S;

$R_3$ is H or $C_1$-$C_6$alkyl or $C_3$-$C_7$cycloalkyl;

$R_4$ and $R_5$ are each H;

m is an integer of 1, 2 or 3;

n is 0 or an integer of 1, 2 or 3;

p is 0 or an integer of 1 or 2;

$R_9$, $R_{10}$, $R_{11}$, and $R_{17}$ are each independently H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;

$R_{12}$, $R_{13}$, $R_{15}$ and $R_{16}$ are each independently H or an optionally substituted $C_1$-$C_4$alkyl group or $R_{12}$ and $R_{13}$ may be taken together with the atom to which they are attached to form a 5- to 7-membered ring optionally containing another heteroatom selected from O, $NR_{18}$ or $SO_p$ or $R_{15}$ and $R_{16}$ may be taken together with the atom to which they are attached to form a 5- to 7-membered ring optionally containing another heteroatom selected from O, $NR_{18}$ or $SO_p$;

$R_{14}$ is a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted; and $R_{18}$ is H or a $C_1$-$C_6$alkyl, $C_2$-$C_6$alkenyl, $C_2$-$C_6$alkynyl, $C_3$-$C_7$cycloalkyl, cycloheteroalkyl, aryl or heteraryl group each optionally substituted;

which process comprises (i) or (ii) below:

(i) cyclizing a compound of formula (VII):

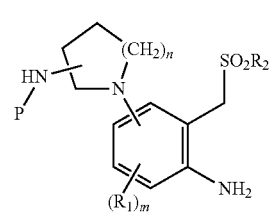

(VII)

wherein, P is a protecting group and $R_1$ and $R_2$ are as defined hereinabove for formula I to form a compound of formula (IX):

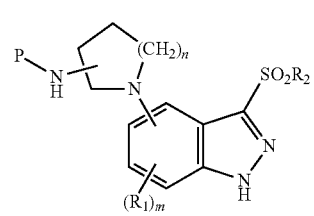

(IX)

and deprotecting said compound of formula (IX) to give the compound of formula (I), wherein $R_3$ of formula I is H;

or (ii) reacting $R_3$-LG with a compound of formula (IX):

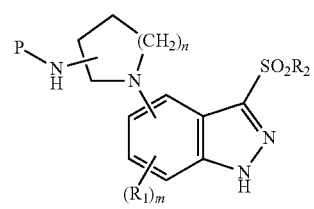

(IX)

wherein $R_3$ is other than H as described hereinabove, LG is a leaving group, P is a protecting group, and $R_1$ and $R_2$ are as defined hereinabove for formula I; and thereafter removing the protecting group to give the compound of formula (I) wherein $R_3$ is other than H as described hereinabove.

20. The process of claim 19, wherein the compound of formula (IX) in (ii) is prepared by cyclizing said compound of said formula (VII) to form the compound of formula (IX).

21. The process of claim 19, wherein the cyclizing step comprises reacting the compound of formula (VII) with sodium nitrate ($NaNO_2$).

22. The process of claim 19, wherein the cyclizing step is performed in the presence of HCl.

23. The process of claim 19, wherein said compound of formula (VII) is prepared by reducing a compound of formula (VI):

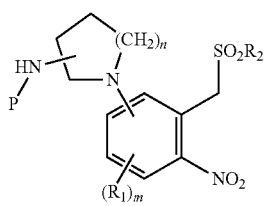

wherein, P is a protecting group, and $R_1$ and $R_2$ are as defined hereinabove for formula I, to form the compound of formula (VII).

24. The process of claim 23, wherein the reducing step is performed in the presence of tin chloride ($SnCl_2$) and HCl.

25. The process of claim 23, wherein the reducing step is performed in the presence of $H_2$ and a palladium catalyst.

26. The process of claim 23, wherein the compound of formula (VI) is prepared by reacting a benzylsulfonyl chloride compound of formula (IV):

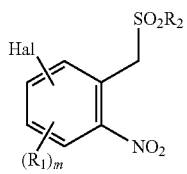

wherein, Hal is a halogen atom and $R_1$ and $R_2$ are as defined hereinabove for formula I, with a protected azacyclylamine of formula V:

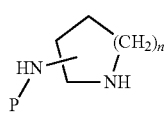

wherein P is a protecting group,
to form the compound of formula (VI).

27. The process of claim 26, wherein the reacting step is performed in the presence of a base.

28. The compound according to claim 10, wherein said compound is selected from the group consisting of (R)-1-(1-isopropyl-3-(naphthalen-1-ylsulfonyl)-1H-indazol-5-yl)pyrrolidin-3-amine; and a pharmaceutically acceptable salt thereof.

29. The composition according to claim 18, wherein said compound is selected from the group consisting of (R)-1-(1-isopropyl-3-(naphthalen-1-ylsulfonyl)-1H-indazol-5-yl)pyrrolidin-3-amine; and a pharmaceutically acceptable salt thereof.

* * * * *